United States Patent [19]

Wattimena

[11] 4,108,917

[45] Aug. 22, 1978

[54] ISOMERIZATION OF TERPENE COMPOUNDS

[75] Inventor: Freddy Wattimena, Amsterdam, Netherlands

[73] Assignee: Shell Oil Company, Houston, Tex.

[21] Appl. No.: 836,808

[22] Filed: Sep. 26, 1977

[30] Foreign Application Priority Data

Oct. 4, 1976 [GB] United Kingdom ............... 41051/76

[51] Int. Cl.² ............................................... C07C 5/26
[52] U.S. Cl. .............................. 260/677 R; 260/675.5
[58] Field of Search ......................... 260/677 R, 675.5

[56] References Cited

U.S. PATENT DOCUMENTS

| 2,325,422 | 7/1943 | Palmer et al. | 260/677 R |
| 2,420,131 | 5/1947 | Goldblatt et al. | 260/677 R |
| 2,444,790 | 7/1948 | Rummelsburg | 260/677 R |
| 3,281,485 | 10/1966 | Blackmore | 260/677 R |
| 3,714,283 | 1/1973 | Rice et al. | 260/675.5 |

*Primary Examiner*—C. Davis

[57] ABSTRACT

Cyclic terpene compounds selected from the class consisting of pinane, alpha-pinene, beta-pinene and mixtures thereof are converted into their corresponding open-chain isomers-e.g., dihydromyrcene, allo-ocimene and myrcene-by thermal isomerization at a temperature of at least 300° C in the presence of a solid material comprising a metal or metal oxide selected from the class consisting of alkali metals, alkaline earth metals, transition metals and mixtures thereof supported on a carrier having a specific surface area in the range of about 0.01 to about 20 m²/g.

9 Claims, No Drawings

ISOMERIZATION OF TERPENE COMPOUNDS

BACKGROUND OF THE INVENTION

This invention relates to an isomerization process for conversion of cyclic terpenes into less cyclic hydrocarbons. More particularly, this invention is directed to an improved thermal isomerization process whereby certain bicyclic terpenes-i.e. pinane, alpha-pinene and beta-pinene are converted in high selectivity into open-chain or acyclic isomers thereof-e.g., allo-ocimene, dihydromyrcene and myrcene-by high temperature reaction in the presence of a solid material comprising a metal and/or metal oxide supported on a carrier having a specific surface area in the range of about 0.01 to about 20 $m^2/g$. The acyclic or open-chain hydrocarbon products of this isomerization are useful as base materials or intermediates in the synthesis of a variety of aroma or perfume chemicals e.g., geraniol, citral, citronellol, linalool, ionones and the like.

It is well known that bicyclic terpenes such as beta-pinene can be thermally isomerized or pyrolyzed to afford varying quantities of acyclic or open-chain isomers. Depending on the bicyclic starting material employed and the reaction conditions selected, the isomerization product typically contains significant amounts of one or more monocyclic hydrocarbons e.g. limonene, in addition to the desired acyclic products. Examples of such thermal isomerization processes include the process described in British Pat. No. 910,879 directed to the preparation of 3,7-dimethyloctadi-1,6-ene (dihydromyrcene) from pinane by vapor phase rearrangement at 360° to 555° C. In the process of the aforementioned British patent, the yield to dihydromyrcene is enhanced by controlling the reactant (pinane) conversion at low levels while maintaining high heat transfer in the reaction tube through the use of copper filler bodies. Another thermal isomerization process for bicyclic terpenes is described in British Pat. No. 1,007,339. In this process, terpene compounds, such as pinane and pinene, are partially pyrolyzed to certain acyclic isomers e.g., ocimene, using short reaction times and high heat transfer rates provided by a reactor containing a heated element immersed in an environment of liquid reactant.

In the foregoing examples and other such thermal isomerization processes, effective heat transfer is quite important due to the relatively high temperatures required for good reactant conversion and the unstable nature of the unsaturated acyclic product obtained at reaction conditions. Thus, while high temperatures are necessary for high conversion, such high temperatures can be tolerated only for rather short residence times without causing considerable reduction in the selectivity with which the bicyclic reactants are converted to the desired open-chain products In this regard, certain shortcomings can be perceived for the thermal isomerization processes previously employed. Due to the relatively high reaction temperatures, carbon is usually deposited during the reaction on the reactor walls and/or on the heat-transferring filler bodies. The removal of the carbon deposits is often difficult and time consuming. Further, while a possibility exists for reducing the severity of the reaction and/or deposition of carbon through the use of a catalyst, previous efforts using catalysts in the thermal isomerization of unsaturated bicyclic hydrocarbons such as alpha-or beta-pinene seem to be directed more towards enhancing the yields or monocyclic products rather than the desired acyclic isomers. For example, U.S. Pat. No. 3,270,075 teaches that the yield of the cyclic product limonene from the cracking of alpha-or beta-pinene may be increased by carrying out the cracking reaction in the presence of a zeolitic metal aluminosilicate catalyst.

SUMMARY OF THE INVENTION

It has now been found that pinene-type bicyclic hydrocarbons can be isomerized to acyclic or open-chained hydrocarbons in good yields while holding the formation of carbon deposits in the reaction to a minimum if the reaction is preformed in the presence of certain low surface area solid materials containing metals and/or metal oxides which exhibit catalytic activity in promoting the isomerization reaction.

Accordingly, in its broadest aspects, the invention may be defined as a process for the conversion of bicyclic terpene compounds selected from the class consisting of pinane, alpha-pinene., beta-pinene and mixtures thereof into open-chain or acyclic isomers thereof which comprises heating the terpene starting material to a temperature of at least 300° C in the presence of a solid material comprising a metal or metal oxide selected from the class consisting of alkali metals, alkaline earth metals, transition metals and mixtures thereof supported on a carrier having a specific surface area in the range of about 0.01 to about 20 $m^2/g$.

DESCRIPTION OF THE PREFERRED EMBODIMENTS

The terpene starting material for the process of the invention may be represented by the formula:

in which X is hydrogen and Y and Z are hydrogen (pinane), or form together a second bond between the carbon atoms to which they are linked (alpha-pinene) or Z is hydrogen and X and Y together form a second bond between the carbon atoms to which they are linked (beta-pinene).

Preferably, pinane is used or a hydrocarbon mixture mainly consisting of pinane with the remainder being a saturated hydrocarbon, e.g., a mixture containing 80% pinane and 20% n-octane. Hydrogenated turpentine is also a suitable feedstock.

It is preferred that the reaction is performed at a temperature not higher than 700° C. While with many solid materials according to the invention, the temperature can suitably be in the range of 350° to 500° C, there are instances where high conversions are achieved at somewhat higher temperatures, e.g., of about 600° C.

Suitable space velocities are usually in the range of 200 to 15,000 1/1h (NPT); higher velocities, although not precluded, do not yield particular advantages.

The carrier for the solid material employed in the invention is suitably a particulate such as an alumina, silica, a silica/alumina or silicon carbide. Preferably, the specific surface area is at most 10 $m^2/g$. Alumina is recommended as the carrier, preferably alpha-alumina and a particular alpha-alumina having a surface area of less than 1 $m^2/g$, for example from 0.1 to 0.5 $m^2/g$.

In addition to the carrier, solid material, according to the invention further contains one or more metals and/or metal oxides which further improve the catalytic activity of the solid materials for the reaction and also enable the regeneration thereof by burning off carbon deposited during the isomerization. Examples of suitable metals are alkali and alkaline earth metals, such as lithium, in the form of oxides, and transition metals, in particular chromium, molybdenum, tungsten, manganese, iron, cobalt, nickel, ruthenium, rhodium, palladium, platinum, copper and silver or mixtures of said alkali and alkaline earth metals and said transition metals. Of these, the noble metals occur in their metallic form, the other metals usually in the form of their oxides. In addition to the above metals promoters, such as oxides of titanium, zirconium and the rare earth metals may also be added. The total amount of metal(s) present may be up to 10% based on the weight of the solid material.

The isomerization process may be carried out using modifications of conventional procedures. Thus, the hydrocarbons, optionally in admixture with a diluent, such as nitrogen or an alkane, may be passed through a tube containing the supported alumina carrier which is heated to the desired reaction temperature. The open-chain products may be recovered, for example by fractional distillation of the reaction product.

The invention is further illustrated in the following Examples.

EXAMPLES I-IX

The cracking reactions were carried out in a heated glass tube reactor, the diameter of which was 40 mm. The heated portion of the reactor was 500 mm long. The temperature inside this heated portion could be measured at three points along the length; in the results given in the Table below the average of these three temperatures is given. In all examples the heated portion contained 21 ml of the catalyst. The composition of the catalysts used was as follows:
A. Alpha-alumina (Norton LA 5556) having a surface area determined by mercury porosity of 0.3 m²/g and containing 10%w metallic silver and 0.3%w of lithium oxide.
B. A catalyst prepared by impregnating a commercially available cobalt/molybdenum/gamma-alumina catalyst with a solution of potassium carbonate in water, followed by drying at 120° C and calcination was: Co 3.0%; Mo 8.3%; K 0.5%w. The surface area of the calcined catalyst was 5.0 m²/g.

In certain of the comparative experiments the catalyst was a gamma-alumina having a surface area of 300m²/g; in other comparative experiments no catalyst was used.
The starting feeds used were:
80% w alpha-pinene in n-octane;
80% w beta-pinene in n-octane;
50% w of a mixture of isomeric pinanes (56% cis; 43.4% trans) in n-octane.

The starting feed was preheated to about 180° C and passed at a fixed rate together with a nitrogen diluent through the heated portion of the reactor containing the catalyst. The product issuing from the reactor was condensed, collected and analyzed by GLC. The results of the Examples together with those of the comparative experiments are set out in the following Table I, in which products are abbreviated as follows:
LIM = limonene
AOC = allo-ocimene
MY = myrcene
DHMY = dihydromyrcene.

TABLE I

| Example | Starting material | Flow rate ml/hour | Nitrogen l/hour | Catalyst | Av. reactor temp. °C |
|---|---|---|---|---|---|
| I | α-pinene | 70 | 9.8 | B | 396 |
| II | " | 70 | 9.8 | B | 372 |
| III | " | 70 | 9.8 | B | 372 |
| Comp. Exp. 1 | " | 70 | 9.8 | none | 387 |
| Exp. 2 | " | 70 | 9.8 | γ-Al₂O₃ | 385 |
| IV | β-pinene | 70 | 9.8 | A | 435 |
| V | " | 70 | 9.8 | B | 402 |
| Comp. Exp. 3 | " | 70 | 9.8 | none | 419 |
| VI | pinane | 70 | 9.8 | A | 479 |
| VII | " | 70 | 9.8 | A | 396 |
| VIII | " | 70 | 9.8 | B | 477 |
| IX | " | 70 | 9.8 | B | 443 |
| Comp. Exp. 4 | " | 70 | 9.8 | none | 467 |
| Exp. 5 | " | 70 | 9.8 | γ-Al₂O₃ | 468 |

| Example | Conversion, % | Selectivity, % LIM | AOC | MY | DHMY |
|---|---|---|---|---|---|
| I | 98.0 | 45.9 | 36.0 | — | — |
| II | 79.3 | 49.4 | 47.3 | — | — |
| III | 94.1 | 48.4 | 40.3 | — | — |
| Comp. Exp.1 | 36.4 | 60.0 | 28.8 | — | — |
| Exp.2 | 100 | 52.6 | trace | — | — |
| IV | 100 | — | — | 83.5 | — |
| V | 80.9 | — | — | 83.7 | — |
| Comp. Exp.3 | 29.4 | — | — | 94.9 | — |
| VI | 50.6 | — | — | — | 69.0 |
| VII | 12.9 | — | — | — | 94.7 |
| VIII | 51.2 | — | — | — | 66.7 |
| IX | 21.2 | — | — | — | 93.5 |
| Comp. Exp.4 | 21.7 | — | — | — | 75.0 |
| Exp.5 | 56.6 | — | — | — | 0 |

EXAMPLES X-XXV

In a stainless steel tube reactor (length 350 mm, diameter 10 mm) provided with a 5 mm thermowell, a series of experiments was performed with a silver on alumina catalyst (catalyst C) containing 8% w metallic silver on alpha-alumina (as for catalyst A). The feed consisted of pinane (purity 99.4%) having a cis/trans ratio of 9:1.

In some of the experiments nitrogen was used as a diluent. The amount of catalyst was 6.6 grams. Conditions and results of the experiments are given in Table II. The products were anlayzed with the aid of GLC.

Table II

| Ex. No. | Conditions Temp. °C | Pinane ml/h | N₂ l/h | Residence time, sec. | Conversion trans % | cis % | overall % | selectivity to dihydromyrcene (DHMY) % |
|---|---|---|---|---|---|---|---|---|
| X | 435 | 17.4 | — | 2.9 | 1.2 | 12.0 | 11.0 | 81.5 |
| XI | 435 | 8.1 | — | 6.2 | 2.1 | 16.2 | 14.9 | 78.7 |
| XII | 460 | 42.8 | — | 1.1 | 4.9 | 33.8 | 31.2 | 79.6 |
| XIII | 460 | 16.3 | — | 3.0 | 10.1 | 49.3 | 45.8 | 72.2 |
| XIV | 460 | 42.0 | 6.0 | 0.58 | 4.5 | 22.9 | 21.2 | 83.6 |
| XV | 460 | 7.6 | — | 6.3 | 16.3 | 65.9 | 61.4 | 59.9 |
| XVI | 500 | 42.6 | 25.7 | 0.21 | 7.1 | 32.9 | 30.6 | 82.4 |
| XVII | 500 | 15.9 | — | 0.29 | 9.2 | 42.6 | 39.5 | 80.8 |
| XVIII | 500 | 15.3 | 5.9 | 0.83 | 20.5 | 77.0 | 71.8 | 71.5 |
| XIX | 500 | 16.6 | — | 2.7 | 33.5 | 86.8 | 81.9 | 57.7 |
| XX | 523 | 36.2 | 25.7 | 0.21 | 21.1 | 75.8 | 70.8 | 75.0 |
| XXI | 523 | 18.2 | 17.5 | 0.33 | 30.2 | 86.7 | 81.5 | 71.0 |
| XXII | 522 | 17.8 | 5.8 | 0.79 | 45.6 | 97.1 | 92.3 | 55.4 |
| XXIII | 542 | 46.5 | 40.9 | 0.14 | 32.8 | 83.6 | 78.9 | 73.0 |
| XXIV | 542 | 41.5 | 28.2 | 0.19 | 35.1 | 91.2 | 86.0 | 70.3 |
| XXV | 542 | 36.0 | 9.9 | 0.42 | 60.2 | 98.5 | 95.0 | 54.3 |

What is claimed is:

1. A process for the conversion of bicyclic terpene compounds selected from the class consisting of pinane, alpha-pinene, beta-pinene and mixtures thereof into open-chain or acyclic isomers thereof which comprises heating the terpene starting material to a temperature of at least 300° C in the presence of a solid material comprising a metal or metal oxide selected from the class consisting of alkali metals, alkaline earth metals, transition metals and mixtures thereof supported on a carrier having a specific surface area in the range of about 0.01 to about 20 m$^2$/g.

2. The process according to claim 1 wherein the terpene starting material is pinane or a hydrocarbon mixture made up principally of pinane with the remainder being a saturated hydrocarbon.

3. The process according to claim 1, wherein the reaction is carried out by heating the terpene starting material to a temperature not exceeding about 700° C.

4. The process according to claim 3 wherein the specific surface area of the carrier does not exceed about 10 m$^2$/g.

5. The process according to claim 4 wherein the specific surface area of the carrier does not exceed about 1 m$^2$/g.

6. The process according to claim 1, wherein the carrier is alpha-alumina.

7. The process according to claim 1 wherein the transition metal is selected from the class consisting of chromium, molybdenum, tungsten, manganese, iron, cobalt, nickel, ruthenium, rhodium, palladium, platinum, copper, silver and mixtures thereof.

8. The process according to claim 7 wherein the transition metal is silver.

9. The process according to claim 7 wherein the transition metal is a mixture of cobalt and molybdenum.

* * * * *